United States Patent [19]
Ray

[11] Patent Number: 5,670,783
[45] Date of Patent: Sep. 23, 1997

[54] AUTOMATED DETECTOR BALANCE

[75] Inventor: Jeffrey S. Ray, Richmond Hts., Ohio

[73] Assignee: Picker International, Inc., Cleveland, Ohio

[21] Appl. No.: 602,127

[22] Filed: Feb. 15, 1996

[51] Int. Cl.⁶ .............................................. G01T 11/166
[52] U.S. Cl. .................... 250/363.05; 250/363.08
[58] Field of Search ................ 250/363.02, 363.05, 250/363.08

[56] References Cited

U.S. PATENT DOCUMENTS

| | | |
|---|---|---|
| 4,216,381 | 8/1980 | Lange . |
| 4,692,625 | 9/1987 | Hanz et al. . |
| 5,047,641 | 9/1991 | Besseling et al. ............. 250/363.05 X |

*Primary Examiner*—Edward J. Glick
*Attorney, Agent, or Firm*—Timothy B. Gurin; John J. Fry

[57] ABSTRACT

A gamma camera and a counterweight are mounted to a support structure. A motor causes the support structure to move about a pivot axis. A controller measures the rate of motion of the support structure and compares that rate to a predetermined rate. The controller causes a second motor to move the counterweight a distance based on the difference between the measured and predetermined rates. The process is repeated until the difference is less than a threshold value. In a second embodiment, the current drawn by the motor is measured. The controller causes the counterweight to move a distance based on the measured current. The support structure is rotated about an axis of rotation to a 90 degree position prior to moving the support structure and to a 0 degree position prior to moving the counterweight.

25 Claims, 8 Drawing Sheets

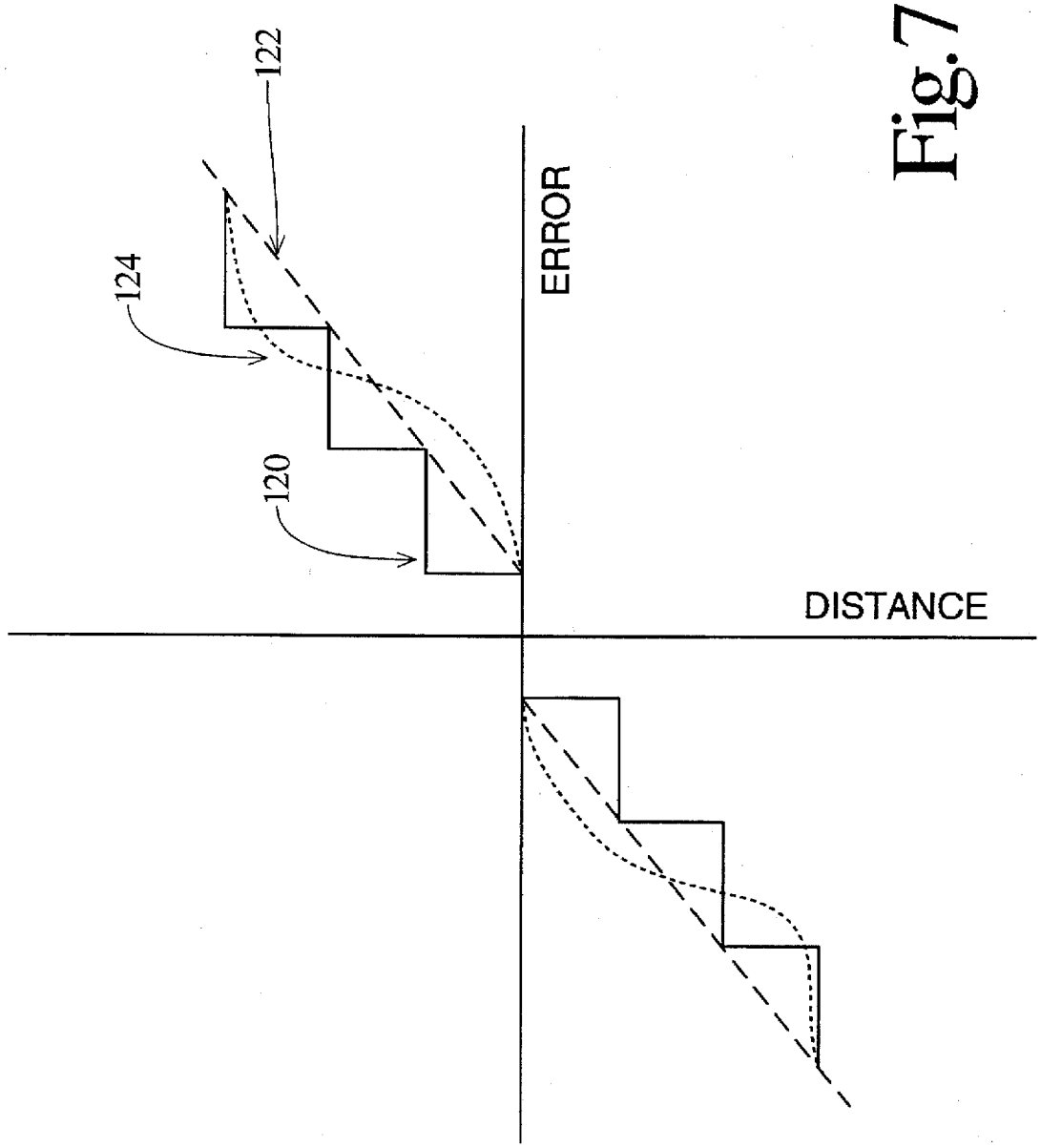

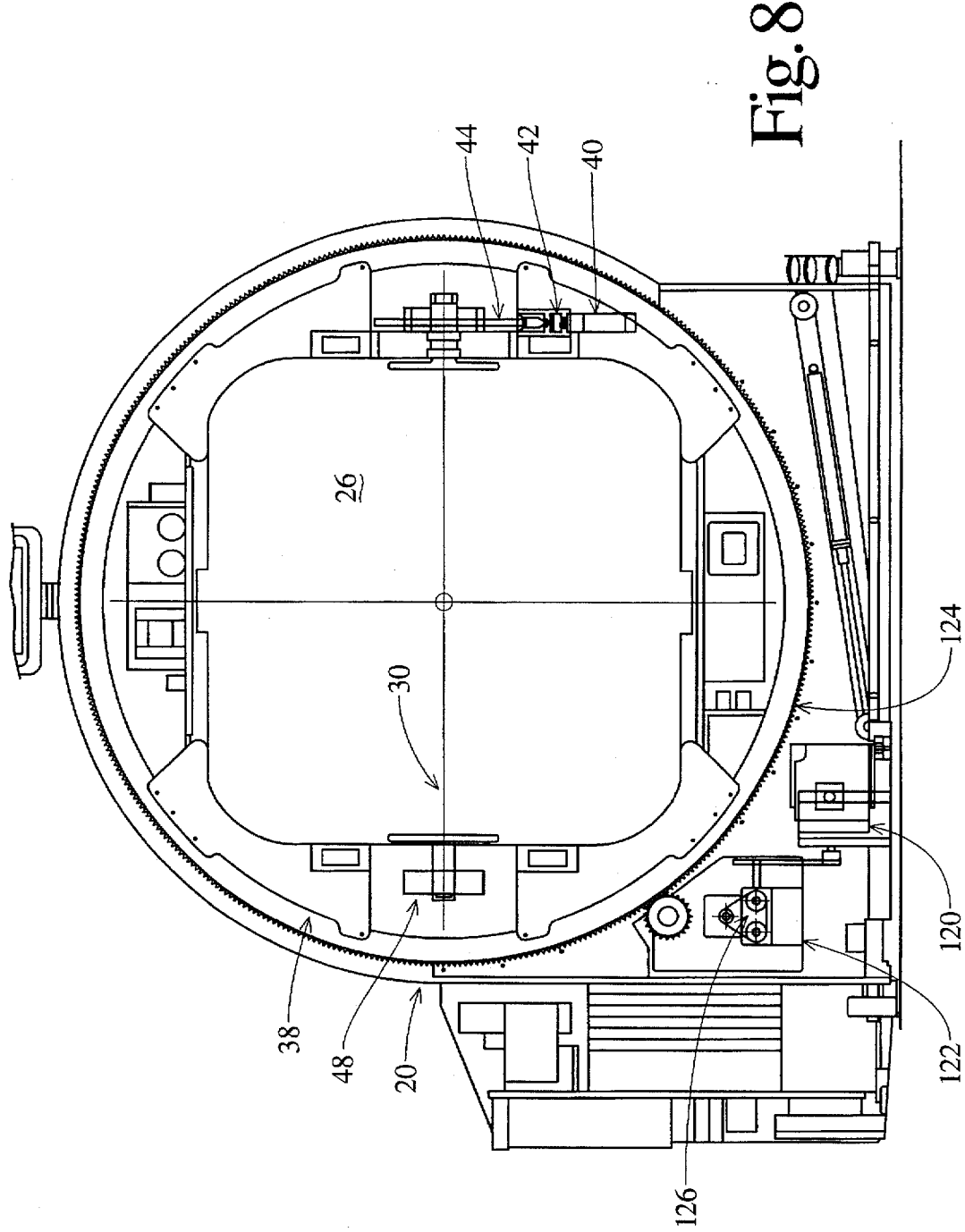

AUTOMATED DETECTOR BALANCE

BACKGROUND

The present invention relates to the art of diagnostic imaging. It finds particular application in conjunction with gamma cameras and will be described with particular reference thereto. It will be appreciated, however, that the invention is applicable to other imaging equipment and methods where automatic, precise balancing of a detector or similar assembly is required.

Gamma or scintillation cameras are often used to measure gamma radiation emitted by a body under examination. One application of nuclear or gamma cameras is in medical imaging, where one or more radionuclides are introduced into a region of interest within a subject. These radionuclides decay, thereby emitting gamma radiation characterized by photons having one or more characteristic energies.

Gamma or scintillation camera heads are placed adjacent to a surface of the subject to monitor and record the emitted radiation. The monitored radiation is then used to create an image representation of the radionuclide distribution within the subject. Production of accurate images requires that the detector head be precisely positioned. In order to minimize image acquisition time, it is also desirable to reduce the time necessary to position the detector head.

A detector head comprises numerous components, including a collimator, a scintillator crystal, photomultiplier robes, and associated electronics. A detector head can weigh upwards of 700 pounds. In order to facilitate the positioning of the relatively heavy detector head, a counterweight of similar mass is often used.

Collimator assemblies suitable for use with detectors are often constructed from lead and can thus constitute a significant fraction of the detector head's total weight. Due to various application requirements, it may be necessary to install one of several different types of collimators on a given detector head. The type of collimator may also be varied from time to time, with a previously installed collimator removed, and a new one installed. It is not unusual for these different types of collimators to weigh from between 150 to 250 pounds. In order to accommodate this rather significant weight variation, it is necessary that the counterweight be adjusted, such as by adding or removing weight or by changing its position.

Heretofore, the position of the counterweight has been varied manually by an engineer or technician to achieve an acceptable balance. As can be imagined, it has been time consuming and laborious to balance the detector within acceptable limits. Even then, the balance determination has been somewhat subjective. As a result, detector performance can deviate from the ideal, particularly in terms of positioning speed and precision. Due to the variations between collimators, this procedure must generally be repeated whenever a collimator is changed as well as when a gamma camera is first installed.

Another prior art technique for automatically adjusting the position of the counterweight involves the use of an electric motor which drives gearing to shift the counterweight until the detector assembly is balanced. Although this arrangement mechanizes the movement of the counterweight, it does not address the shortcomings noted above. As an improvement to the aforementioned arrangement, it is known to use limit switches to provide a signal which stops the electric motor when the counterweight reaches a predetermined position. This arrangement, however, still requires that the limit switches be accurately located and thus remains subject to the shortcomings mentioned above. This arrangement also fails to account for variations in individual collimators and, as a practical matter, restricts automatic operation to collimators having one of a relatively few predetermined weights.

SUMMARY

The instant invention addresses these shortcomings, and others. It provides a precise, automatic, and efficient balancing apparatus and method which is particularly well suited for use with gamma or scintillation cameras.

In accordance with the present invention, an apparatus for balancing the weight of a gamma camera comprises a support structure comprising a detector and a counterweight and having a center of mass, a means for moving the support structure, means for measuring the velocity of the support structure, means for comparing the measured velocity to a desired velocity, and means for adjusting the center of mass of the support structure based on the difference between the measured and desired velocities.

According to a more limited aspect of the present invention, the means for moving causes the support structure to move in a first direction, and the center of mass is adjusted accordingly. According to another aspect of the invention, the means for moving causes the support structure to move in first and second directions, and the means for adjusting adjusts the center of mass based on the difference between the measured and desired speeds in the first and second directions.

According to yet another aspect of the invention, the means for adjusting the mass of the support structure includes a counterweight movably mounted to the support arm. The counterweight is moved a distance which is a function of the difference between the actual and desired velocities. The counterweight is adjusted using a staircase, linear, or non-linear function, or a combination thereof.

According to another aspect of the invention, a device for balancing the weight of a gamma camera includes a support structure which includes a detector and a counterweight and having a center of mass. The device further comprises means for determining and adjusting the center of mass. The means for determining and adjusting the center of mass further includes a means for moving the support structure and means for determining the force required to move the support structure.

According to a more limited aspect of the invention, the support structure is moved by a motor. The force is determined by measuring the velocity of the support structure or the current drawn by the motor.

It will be appreciated that the present invention provides an automatic detector balancing apparatus and method which addresses the shortcomings present in the prior art. In particular, the present invention balances the detector with a minimum of intervention by the operator or technician. The present invention similarly provides an accurate balance which less susceptible to subjective factors such that precise detector positioning is facilitated.

DRAWINGS

FIG. 7 is a graphical depiction of counterweight motion as related to the difference between actual and desired support arm speeds.

FIG. 8 is a view of an inner gantry according to the present invention.

DESCRIPTION

Figure 1:
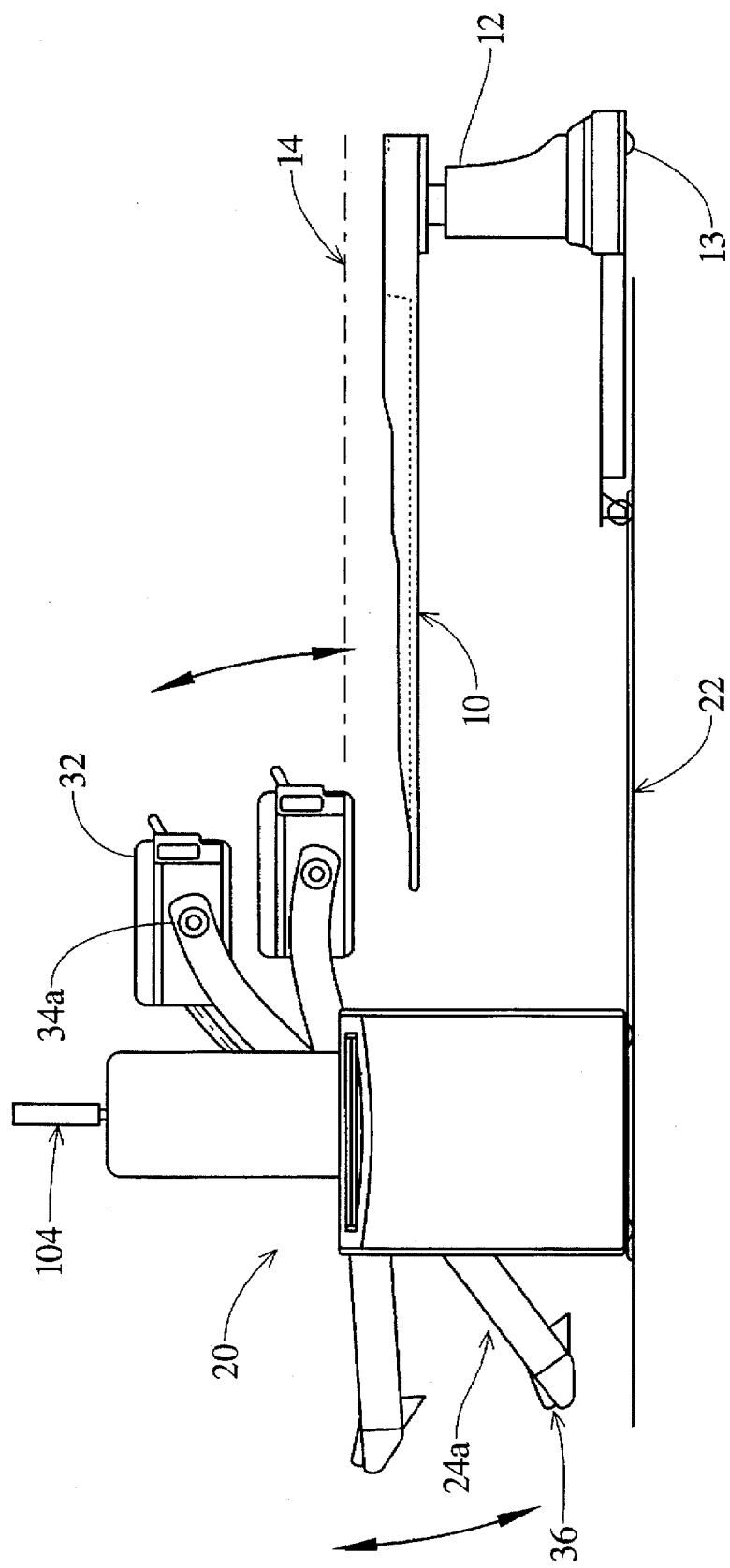
FIG. 1 is a side view of a gamma camera according to the present invention.
Figure 2:
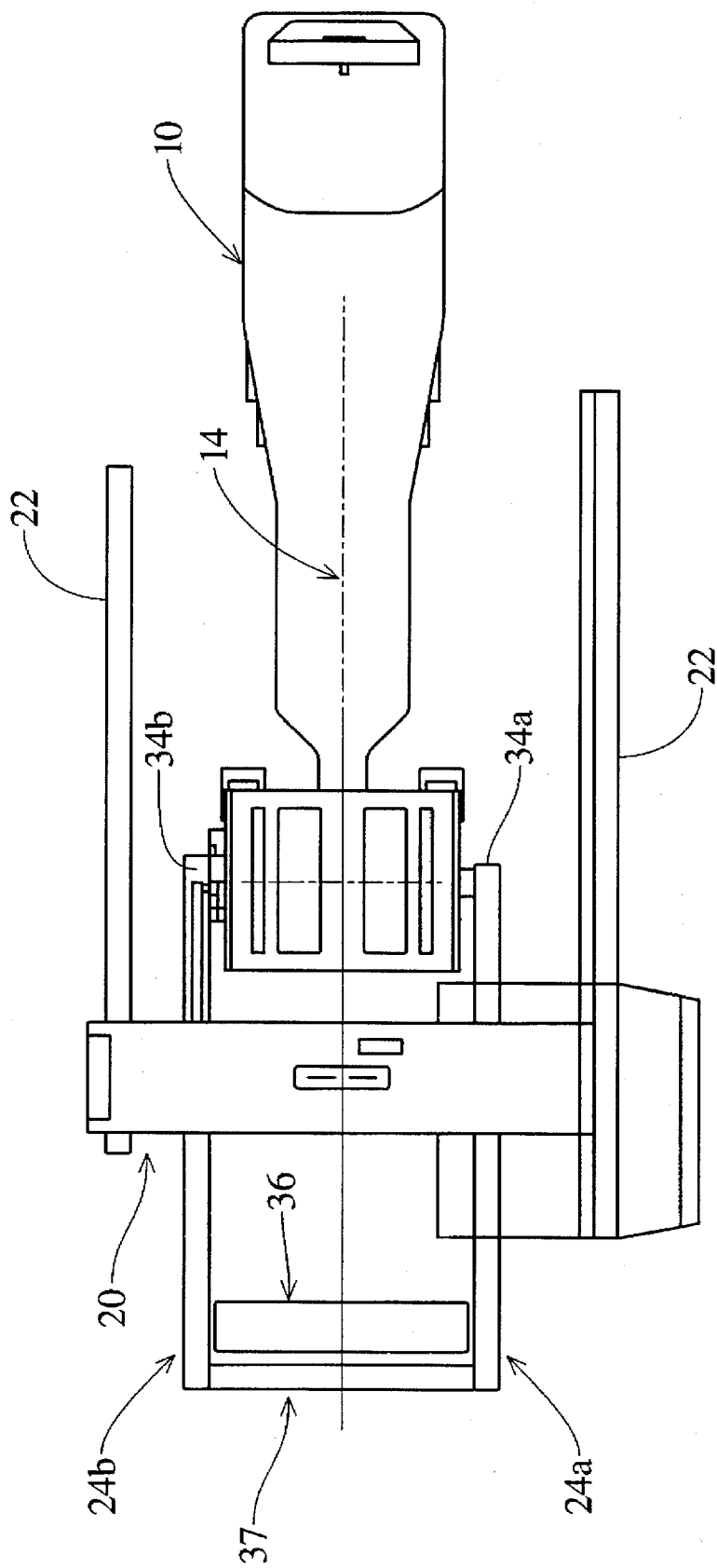
FIG. 2 is a top view of a gamma camera according to the present invention.

With reference to FIGS. 1, and 2, a subject support or table 10 is mounted on a vertical support 12. The table can be moved up and down so that the subject can be positioned along a desired longitudinal axis 14. The table 10 is mounted on wheels to permit the table 10 to be moved.

An outer gantry 20 is movably mounted on tracks 22 which permit the outer gantry 20 to be moved in a direction parallel to the longitudinal axis 14. An inner gantry 38 is rotatably mounted within the outer gantry 20 such that its axis of rotation coincides with axis 14. The inner gantry 38 defines an inner opening or aperture 26 through which the table 10 and a patient (not shown) supported thereon can be passed. A generally circular imaging region is defined within the aperture 26.

Figure 4:
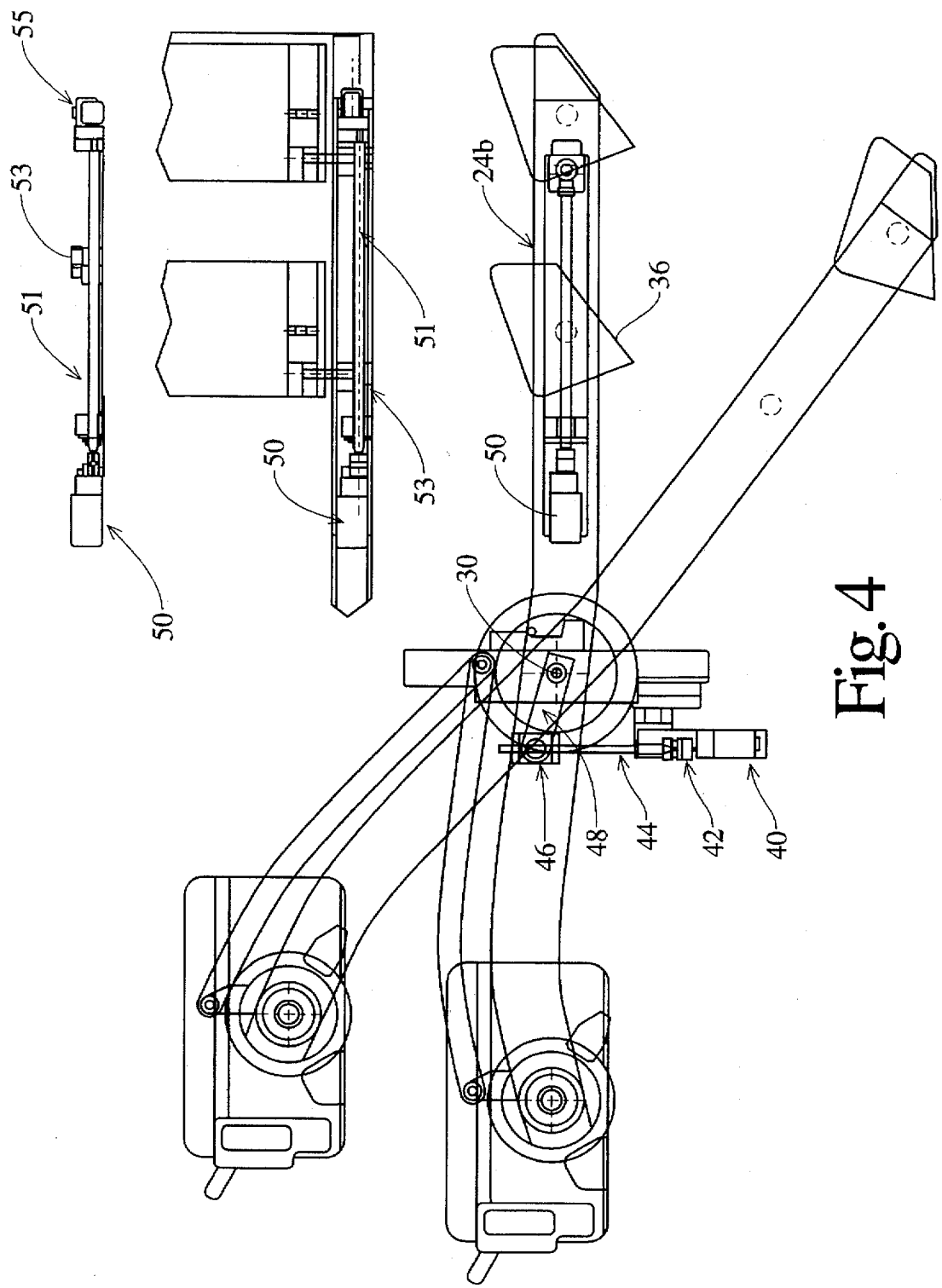
FIG. 4 is a side view of support arms and associated structure according to the present invention.

Support arms 24a and 24b are pivotally mounted along an axis 30 such that the support arms can be pivoted within a range of positions. It will be appreciated that FIGS. 1 and 4 show the support arms 24a and 24b in two representative positions, the first near to horizontal and the second at approximately a 45 degree angle from the horizontal. A gamma camera or detector head 32 is in turn pivotally mounted to the support arms 24a and 24b at pivot points 34a and 34b such that the face of the detector 32 can be maintained at a desired angle with respect to the longitudinal axis 14. A counterweight 36 is movably mounted between the support arms 24a and 24b on the other side of the axis 30 from the detector 32. A rigid support member 37 connects the support arms 24a and 24b.

Figure 3:
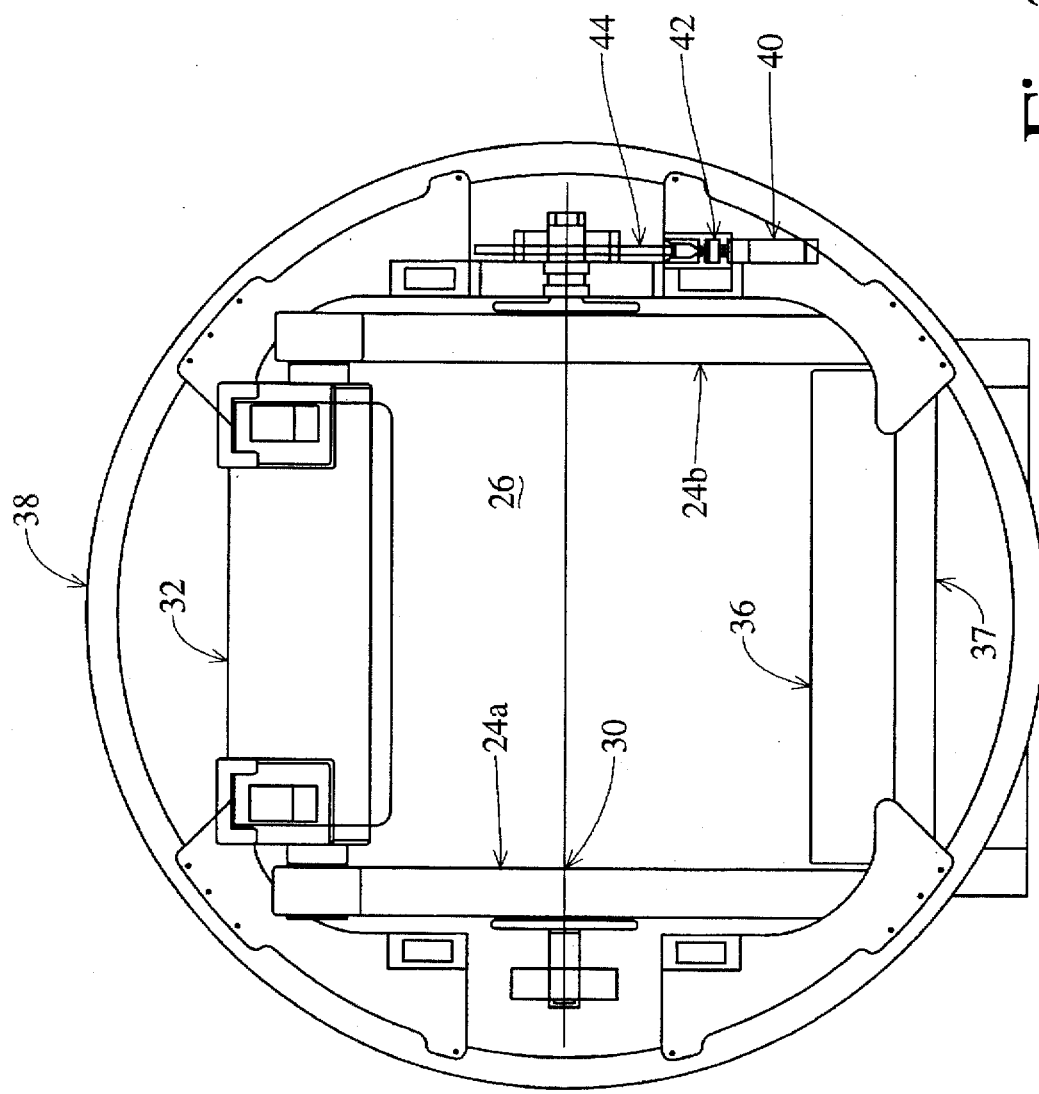
FIG. 3 is a front detail view of an inner gantry according to the present invention.

With reference to FIGS. 3 and 4, a DC motor 40 or other motive device is stationarily mounted with respect to the inner gantry 38. The output shaft of the DC motor 40 is connected through an electromagnetic clutch 42 to a rotating shaft 44 which in turn engages a linear actuator 46. Rotation of the shaft 44 causes the linear actuator 46 to move along the shaft 44 in a direction determined by the direction of rotation. The actuator is in turn connected to a radius drive arm 48 connected to support arm 24b. Operation of the motor 40 causes the support arms 24a and 24b to move or pivot about axis 30. The position of the support arms 24a and 24b is determined using a conventional position detection arrangement such as a potentiometer and/or quadrature encoder in communication with support arm 24a as shown generally in FIG. 3. The foregoing arrangement will generally be referred to as the radius drive mechanism.

Operation of the radius drive mechanism is improved if the weight of the support structure comprising the detector 32, the support arms 24a and 24b, and the counterweight 36 are balanced with respect to the pivot axis 30. In particular, a less powerful motor 40 and other drive components are required compared to an unbalanced arrangement. Careful balancing provides other advantages such as enhancing the radius drive's positional accuracy and increasing attainable positioning speeds.

As compared to an unbalanced situation, the torque required to move the support structure will be reduced when the center of mass is near the pivot axis 30. Stated another way, the center of mass can be estimated by determining the torque needed to move the support structure. As known to those skilled in the art, a DC motor supplied by a constant voltage will, over a range of output torque, operate at a substantially constant speed. In turn, the current drawn by the motor is generally proportional to output torque. Above a load torque which is related to the design and size of the motor, the speed of the motor will vary with changes in load. Thus, it will be appreciated that the speed at which the support structure moves is indicative of the force required to move the support structure and hence the support structure's center of mass. The current drawn by the motor provides a similar indication.

With reference to FIG. 4, the counterweight 36 is movably mounted along the longitudinal areas of the support arms 24a and 24b. FIG. 4 shows the counterweight 36 in two representative positions—a relatively outer position nearer to the end of the support arms 24a and 24b and a relatively inner position nearer to the pivot axis 30. A DC motor 50 or other motive device is mounted within a cavity in the support arm 24b. Connected to the output shaft of the motor 50 is a conventional jackscrew 51 and actuator 53. The counterweight receives further mechanical support from guides disposed on the inner surface of the support arms 24a and 24b. The position of the counterweight 36 is determined using a conventional position sensor 50 such as a potentiometer and/or quadrature encoder. Operation of the motor 50 thus causes the counterweight 36 to move along the longitudinal axes of the support arms 24a and 24b in a direction determined by the direction of rotation of the motor 50.

With reference to FIG. 8, a motive device 120 such as an AC motor is stationarily mounted with respect to the outer gantry 20. The output shaft of the motor 120 is connected through an electromagnetic clutch and gearing 122 to teeth 124 disposed on the outer surface of the rotating inner gantry 38. The position of the inner gantry 38 is determined using a position sensor 126 such as a quadrature encoder and/or potentiometer arrangement. Operation of the motor 120 thus causes the inner gantry 38 to rotate in a direction determined by the direction of rotation of the motor 120.

Although the foregoing description is with respect to the preferred embodiment, it will of course be appreciated that the invention can be used with other positioning means as are well known in the art. For example, other motive elements, including AC induction and synchronous motors, stepper motors, and brushless DC motors as well as pneumatic and hydraulic actuators can be used. Similarly, the invention can be used with alternate gearing and coupling arrangements without deleteriously impacting the principles of the invention. It should also be noted that alternate position sensors, such as limit switches, magnetic sensors, optoelectronic sensors, ultrasonic locators, and the like could be used.

Figure 5:
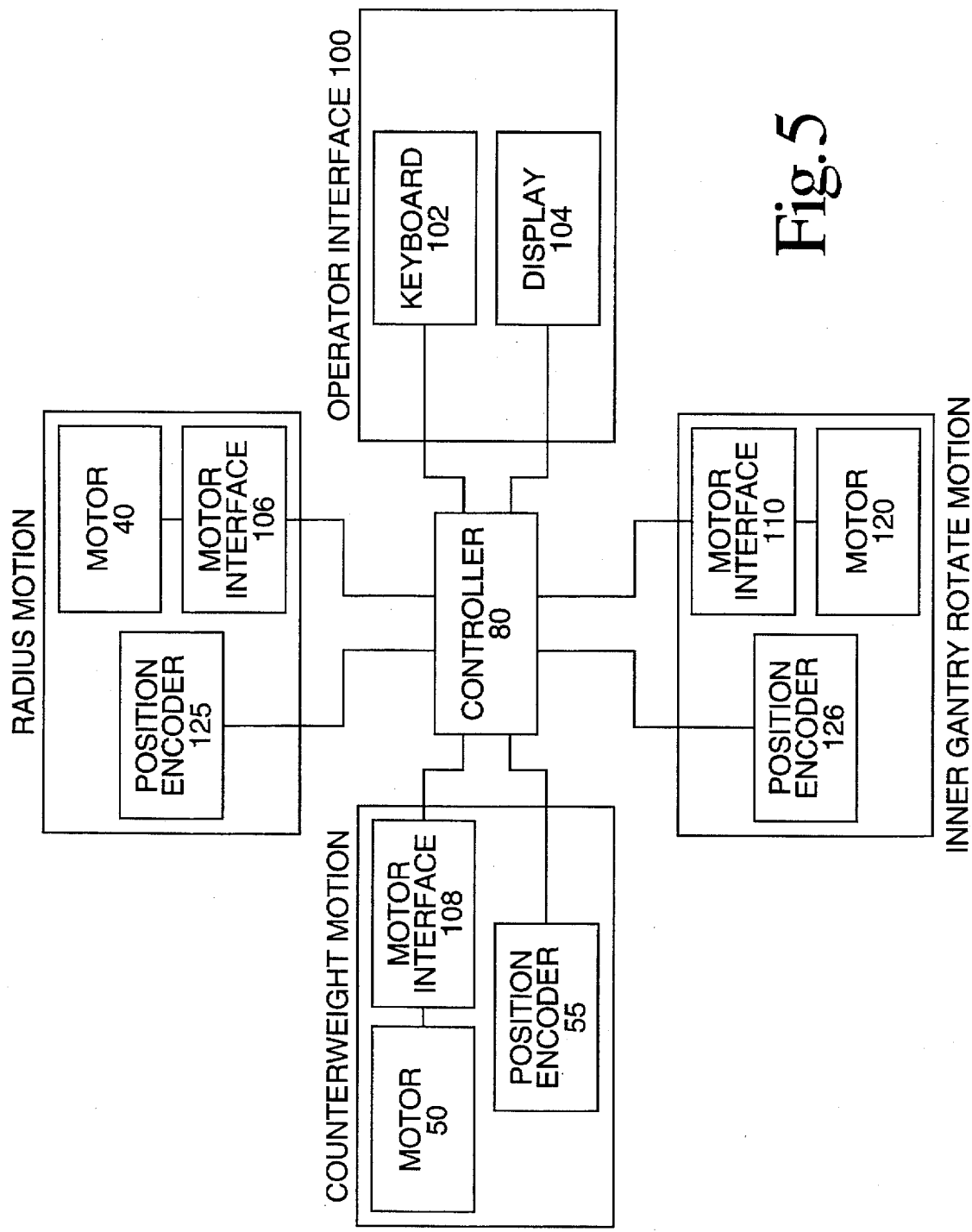
FIG. 5 is a block diagram of illustrating the functional relationships of certain aspects of the present invention.

With reference to FIG. 5, a controller 80 is in operative communication with the radius drive mechanism, the counterweight motion mechanism, and the inner gantry rotation mechanism. The controller 80 is also in communication with an operator interface 100 which preferably comprises an operator input device 102 such as a membrane keyboard 102 and a display 104. To initiate radius motion, counterweight motion, and inner gantry rotation, the controller sends appropriate signals to motor interfaces 106, 108, and 110, respectively. The respective motor interfaces 106, 108, and 110 then provide appropriate voltage and current signals to the motors 40, 50, and 120. Position sensors or encoders 125, 55, and 126 produce signals indicative of the respective positions.

Figure 6:
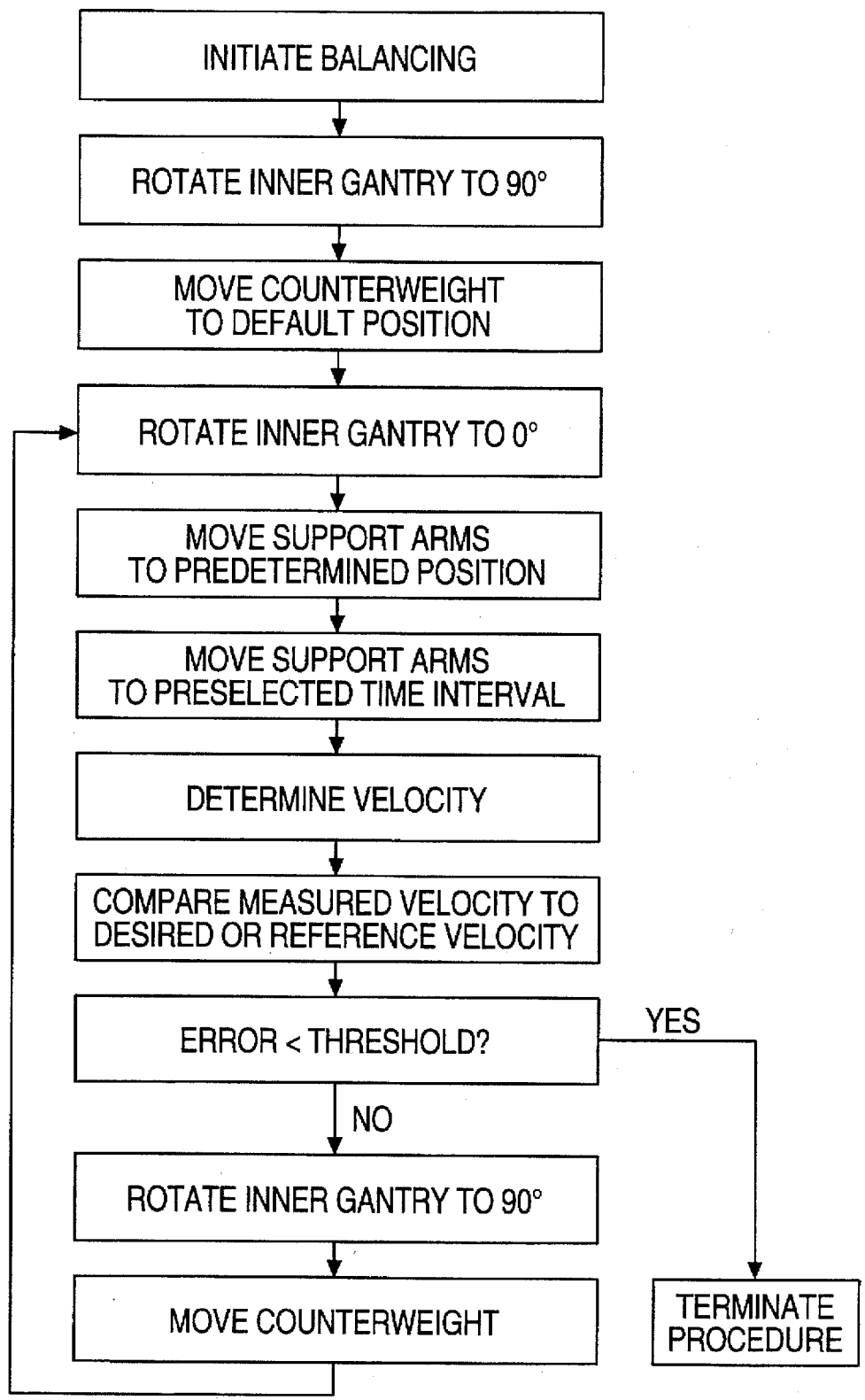
FIG. 6 is a block diagram of a method according to the present invention.

With reference to FIG. 6, the operator initiates a balancing operation through the operator interface 100. Balancing of the detector proceeds as set forth below and in FIG. 6.

The inner gantry 38 is first rotated to a position referred to the 90 degree position wherein the support arm pivot axis 30 is substantially vertical.

The counterweight 36 is then moved to a default position along the axes of the support arms 24a and 24b. The default position selected so that the center of mass of the support structure comprising detector 32 (as fitted with a representative collimator), the counterweight 36, and the support arms 24a and 24b is at approximately the support arm pivot axis 30. Preferably, a plurality of default positions are implemented, the default positions each taking account of an expected collimator weight. The collimators are fitted with electrical jumpers which are in electrical contact with connectors on the detector 32. The connectors in the detector are in turn in electrical communication with the controller 80. Depending on the configuration of the jumpers, the type of collimator is determined by the controller 80 and the appropriate approximate default position is selected automatically.

The inner gantry 38 and thus the support structure is then rotated such that the support arm pivot axis 30 is substantially horizontal, a position referred to as the 0 degree position. The support arms 24a and 24b are then moved to a predetermine position, for example such that the face of the detector 32 is 20 cm above the isocenter of the imaging region.

The support arms are then moved or pivoted about the support arm pivot axis 30 so that the counterweight 36 is moved in the down direction for a preselected time interval, for example 10 seconds. The change in the angular position of the support arms 24a and 24b as indicated by the radius position sensor or encoder 125 is used to determine the average angular velocity of the support arms 24a and 24b over the preselected time interval.

This measured velocity is than compared to a reference velocity which was determined in advance when the detector and counterweight were known to be precisely balanced, or by calculating the angular velocity based on the motor rated output speed and the associated gearing. If the difference in the measured and desired velocities is less than a predetermined threshold value, the procedure is terminated. If not, the counterweight 36 is then moved a distance determined based on the difference between the measured and desired velocities. The direction of movement is determined based on the direction of the error. If the actual velocity is greater than the desired velocity, the counterweight 36 is moved in the in direction. If the actual velocity is less than the desired velocities, the counterweight 36 is moved in the out direction. The balancing procedure is then repeated until the difference between the actual and desired velocities is less than the predetermined threshold. It will be appreciated that the balancing procedure results in the center of mass of the combined detector 32, support arm 24a and 24b, and counterweight 36 structure being nearer to the pivot axis 30. It should be noted that the predetermined threshold is determined in advance so as to provide an acceptable detector balance while minimizing hunting in determining the counterweight 36 position.

With reference to FIG. 7, the counterweight 36 is advantageously moved a distance determined using a staircase function 120. That is, if the difference in velocity is within a first range of values, the counterweight is moved a first distance, and so on. Alternately, the position can be adjusted using a linear 122 or a non-linear function 124, and aspects of the various functions can be combined. The functions are preferably, but not necessarily, symmetrical about the zero error point It will be appreciated that the foregoing steps are preferably conducted under the control of the controller 80.

In an alternate embodiment of the present invention, the method can be such that the radius drive velocity is measured when the counterweight 36 is moved in the upward direction, with the direction of movement of the counterweight varied accordingly. Additionally, the counterweight 36 can be moved in both directions and the errors averaged. This average error signal can then be used to vary the counterweight position.

In yet another alternate embodiment, it is not necessary that the radius drive be moved for a predetermined time period. Thus, for example, the radius drive can be moved a predetermined distance, with the time needed to move that distance measured, and the average speed computed accordingly. It is of course possible to use appropriate limit switches to determine when the distance has been traversed. Alternatively, it is also possible to measure the speed directly.

Similarly, it is possible to move the counterweight without regard to position. Thus, rather than moving the counterweight a predetermined distance, it is possible to move the counterweight for a predetermined time period which is determined in accordance with FIG. 7, with time being substituted for distance.

In yet another embodiment of the invention, it is possible to adjust the center of mass based on the torque required to pivot the detector structure. A signal indicative of the torque, such as the current drawn by the motor, is substituted for the speed measurement and is compared to a current level indicative of a balanced condition. The center of mass is adjusted based on the error using the method set forth above.

In yet another embodiment, the supper structure and detector can be moved in two directions, preferably up and down. When the support structure is balanced about the pivot axis 30, the torque required to rotate the detector in both directions will be approximately equal. Hence, the velocity in each direction will be approximately equal. The velocity in each direction is compared, and the center of mass is adjusted until the difference between the velocities is minimized or less than a threshold. This technique can also be implemented by comparing the current drawn by the motor in the two directions, with the center or mass adjusted accordingly.

Although the invention has been described with respect to its preferred embodiment Obviously, modifications and alterations will occur to others upon reading and understanding the foregoing description. It is intended that the invention be construed as including all such modification and alterations insofar as they come within the scope of the appended claims or their equivalents.

What is claimed is:

1. An apparatus for balancing the weight of a gamma camera, the apparatus comprising:

a support structure comprising a detector and a counterweight and having a center of mass;

means for moving the support structure;

means for measuring the velocity of the support structure; and means for adjusting the center of mass of the support structure based on the measured velocity.

2. The apparatus of claim 1 further comprising means for comparing the measured velocity to a desired velocity, wherein the means for adjusting adjusts the center of mass of the support structure based on the difference between the measured and desired velocities.

3. The apparatus of claim 1 wherein
the means for moving moves the support structure in a first direction; and
the means for measuring measures the velocity of the support structure in the first direction.

4. The apparatus of claim 3 wherein
the means for moving moves the support structure in a second direction;
the means for measuring measures the velocity of the detector in the second direction; and
the means for adjusting adjusts the center of mass based on the measured velocities in the first and second directions.

5. The apparatus of claim 1 wherein the means for adjusting comprises a counterweight movably mounted with respect to the support structure.

6. The apparatus of claim 5 wherein the position of the counterweight is adjusted using a staircase function.

7. The apparatus of claim 5 wherein the position of the counterweight is adjusted using a linear function.

8. An apparatus for balancing the weight of a gamma camera, the apparatus comprising:
a support structure comprising a detector and a counterweight and having a center of mass;
motor means for moving the support structure;
means for determining the torque supplied by the motor means required to move the support structure; and
means for adjusting the center of mass of the support structure based on the determined torque.

9. The apparatus of claim 8 wherein the center of mass is adjusted using a staircase function.

10. The apparatus of claim 8 wherein the center of mass is adjusted using a non-linear function.

11. The apparatus of claim 8 wherein the means for adjusting comprises a weight movably mounted to the support structure.

12. An apparatus for balancing the weight of a gamma camera, the apparatus comprising:
a support structure comprising a detector and a counterweight and having a center of mass;
means for moving the support structure;
means for determining the force required to move the support structure; and
means for adjusting the center of mass of the support structure based on the determined force.

13. The apparatus of claim 12 wherein the means for moving comprises a motor and the means for determining the force required to move the support structure utilizes a parameter indicative of the torque supplied by the motor.

14. The apparatus of claim 13 wherein the parameter is the current drawn by the motor.

15. The apparatus of claim 13 wherein the parameter is the velocity of the support structure.

16. The apparatus of claim 12 wherein the means for determining comprises means for measuring the velocity of the support structure.

17. The apparatus of claim 12 wherein the support structure further comprises a support arm and the means for adjusting comprises a counterweight movably mounted to the support arm.

18. In a gamma camera, a method of balancing a support structure comprising a detector, the support structure having a center of mass, the method comprising the steps of:
causing a means for moving the support structure to move the support structure;
measuring the velocity of the support structure; and
adjusting the center of mass based on the measured velocity.

19. The method of claim 18 wherein means for moving is a motor and the step of causing comprises the step of causing the motor to move the support structure in a fast direction.

20. The method of claim 19 wherein the step of causing further comprises the step of causing the motor to move the support structure in a second direction.

21. The method of claim 18 wherein the step of adjusting comprises the step of moving a counterweight disposed on the support structure.

22. The method of claim 18, wherein the support structure comprises a counterweight, further comprising the steps of
rotating the support structure to a 0 degree position prior to moving the support structure;
moving the counterweight to a default position; and
rotating the detector to a 90 degree position prior to moving the counterweight.

23. The method of claim 18 wherein the step of measuring the velocity comprises the steps of
moving the support structure for a time interval; and
measuring the distance moved by the support structure during the time interval.

24. In a gamma camera, a method of balancing a support structure comprising a detector, the support structure having a center of mass, the method comprising the steps of:
causing a motor to move the support structure;
measuring the current drawn by the motor; and
adjusting the center of mass based on the current drawn by the motor.

25. The method of claim 24 wherein the step of adjusting comprises the step of moving a counterweight a distance which is a function of the measured current.

* * * * *